United States Patent
Campbell et al.

(10) Patent No.: US 7,182,820 B2
(45) Date of Patent: Feb. 27, 2007

(54) METHODS AND APPARATUS FOR CLEANING A HEARING AID DEVICE

(75) Inventors: Don E. K. Campbell, Winter Springs, FL (US); Srinivas Chari, Longwood, FL (US)

(73) Assignee: Magnatone Hearing Aid Corporation, Casseberry, FL (US)

( * ) Notice: Subject to any disclaimer, the term of this patent is extended or adjusted under 35 U.S.C. 154(b) by 216 days.

(21) Appl. No.: 10/249,554

(22) Filed: Apr. 17, 2003

(65) Prior Publication Data

US 2003/0196687 A1 Oct. 23, 2003

Related U.S. Application Data

(60) Provisional application No. 60/373,114, filed on Apr. 17, 2002.

(51) Int. Cl.
*B08B 7/00* (2006.01)

(52) U.S. Cl. .................. 134/19; 134/1; 134/6; 134/33; 134/35; 134/42; 134/61; 134/201; 34/209; 34/210; 34/218

(58) Field of Classification Search .............. 134/1, 134/6, 19, 35, 33, 42, 61, 201; 34/209, 210, 34/218

See application file for complete search history.

(56) References Cited

U.S. PATENT DOCUMENTS

| 5,133,016 A | 7/1992 | Clark ................. 381/69.2 |
| 5,640,783 A | 6/1997 | Schumaier ............. 34/219 |
| 5,852,879 A * | 12/1998 | Schumaier ............. 34/80 |
| 6,399,920 B1 * | 6/2002 | Guinn ................ 219/386 |
| 2004/0244215 A1 * | 12/2004 | Greenspan et al. ......... 34/80 |

FOREIGN PATENT DOCUMENTS

DE 200 07 224 U1 4/2000
JP 2001-258099 A 9/2001

* cited by examiner

*Primary Examiner*—Zeinab El-Arini
(74) *Attorney, Agent, or Firm*—Ice Miller LLP (57) ABSTRACT

Methods and apparatus for cleaning hearing aid devices are disclosed. Drying is facilitated in hearing instruments through a novel combination of heater and desiccant in an essentially closed system. Greater efficiency is obtained by minimizing the volume of gas, e.g., air, requiring moisture extraction.

29 Claims, 5 Drawing Sheets

METHODS AND APPARATUS FOR CLEANING A HEARING AID DEVICE

CROSS REFERENCE TO RELATED APPLICATIONS

The present application claims priority to U.S. Provisional Patent Application Ser. No. 60/373,114 filed Apr. 17, 2002, the contents of which are incorporated herein by reference.

BACKGROUND OF INVENTION

1. Field of the Invention

The invention relates to methods and apparatus for cleaning hearing aid devices.

2. Description of Related Art

A hearing aid patient relies on a hearing aid device, and thus its components, to reliably function. Hearing aid devices comprise numerous sensitive electronic components. These components may include a receiver, microphone, volume control, potentiometers, contacts, and circuitry.

Hearing aid devices are subject to a moist environment. Moisture alone may negatively impact device performance and longevity. Moisture also aggravates the buildup up ear wax, dirt, and grime, which may also deteriorate performance and longevity.

Untreated moisture may, for example, cause corrosion on contacts, potentiometers, circuitry, and wires, condensation on screens or diaphragms in the microphone/receiver, and/or loss of sensitivity of or change in the frequency response of the microphone/receiver. Further, untreated moisture and buildup may lead to infections.

Reducing moisture content and/or facilitating the removal of buildup assists in the reliable functionality, maintainability, cleanliness, and longevity of hearing aid devices.

Hearing aid devices may be cleaned manually and/or automatically. Prior art automatic cleaning devices disclose open systems, unnecessarily complex closed systems having unnecessarily large volumes of gas requiring moisture extraction, and/or bulky designs, resulting in unnecessarily expensive products, electricity consumption, inefficient operation, and/or a lack of portability.

Various hearing aids and methods for their cleaning and drying have been disclosed to the public. For example, U.S. Pat. No. 5,133,016 (issued Jul. 21, 1992) offers a hearing aid having a replaceable container of desiccant material replaceably mounted therein. The desiccant is preferably associated with the battery to allow simultaneous replacement of each.

U.S. Pat. No. 5,640,783 (issued Jun. 24, 1997) and U.S. Pat. No. 5,852,879 (continuation-in-part of U.S. Pat. No. 5,640,783; issued Dec. 29, 1998) suggest the use of a chamber for recirculating gas past a heater and a moisture sensitive item. The chamber is substantially sealed, and contains a desiccant mounted within the chamber. The circulation of gas within the chamber is caused by a fan.

DE 200 07 224 U1 (Apr. 20, 2000) describes a dryer having an inlet for airflow that passes over an electrical heating element before passing to an outlet in the base of the component container. The containers can hold small electronic components such as hearing aids.

JP 2001-258099 A (Sep. 21, 2001) suggests a hearing aid case comprising a charcoal sheet on one of its inner side surfaces. The sheet is accommodated on a storage board that can be inserted or detached along a groove provided in the case.

There remains a need for a cost effective, efficient, and portable automatic hearing aid cleaning apparatus. The present invention is directed to overcoming, or at least reducing the effects of, one or more of the problems set forth above.

SUMMARY OF INVENTION

Methods and apparatus for cleaning a hearing aid device are disclosed. Drying is facilitated in hearing instruments through a novel combination of heater and desiccant in an essentially closed system. Greater efficiency is obtained by minimizing the volume of gas, e.g., air, requiring moisture extraction.

In other embodiments a hearing aid device is positioned above a heating element and below a desiccant. In another embodiment the hearing aid cleaning apparatus is compartmentalized, such that heat enters the hearing aid compartment through convection from the wall of the heating element compartment and rises into the desiccant compartment. In another embodiment the heating element may deliver either continuous or pulse heat convection. In another embodiment the hearing aid cleaning apparatus has an adjustable climate control for adaptation to different patients and/or environments.

In other embodiments the hearing aid cleaning apparatus may include a continuous, periodic, or temporary ionizer for quick moisture removal and disinfection. In one embodiment of an ionizer the hearing aid cleaning apparatus may include ozone or an anti-bacterial gas. In another embodiment an electrostatic force may be used to charge gas molecules.

The hearing aid cleaning apparatus can include a UV light source, or can be connected to a UV light source. Short term exposure of the compartment containing the hearing aid to UV light can aid in disinfecting the hearing aid.

In other embodiments the hearing aid cleaning apparatus can include a battery charger for recharging hearing aid rechargeable battery(ies). In one embodiment the battery charger is a separate device which can be attached to and removed from the hearing aid cleaning apparatus. In other embodiments the hearing aid cleaning apparatus can include storage space for supplies, e.g., wax brush, spare batteries.

In other embodiments the hearing aid cleaning apparatus can include a continuous, periodic, or temporary vibrator to assist in loosening buildup. In another embodiment the device can include a continuous, periodic, or temporary vacuum.

In another embodiment the desiccant can only be exposed when the system is closed such that it is not unnecessarily exposed to moisture when the device is opened, perhaps for extended periods of time. In other embodiments the desiccant resides in its own chamber which is only exposed to the hearing aid chamber. In another embodiment the separation between the desiccant and hearing aid contains a plurality of apertures to allow gas communication.

In another embodiment the hearing aid cleaning apparatus contains a transparent cover over the desiccant where the desiccant changes color as it become saturated; thereby allowing the patient to determine the status of the desiccant. In another embodiment the desiccant can be accessed without opening the closed system. In one such embodiment a sleeve or closing device between the desiccant and hearing aid chambers can seal the system before or while the desiccant is being accessed.

In another embodiment the volume of desiccant is variable. In another embodiment the device can include centrifugal support to direct buildup out of hearing aid devices. In another embodiment the device can include a sound port or tubing charger, i.e., an electrical stimulus, meant to vibrate or electrically oppose buildup. In another embodiment the device can include a rechargeable or wireless power supply, e.g., solar cell, batteries expendable or rechargeable. In one such embodiment solar cells can charge rechargeable batteries. In another embodiment the device can include a rapid cooling chamber meant to facilitate loosening of buildup through contraction-expansion. In another embodiment the device can include alternative power supplies to increase utility and portability, e.g., battery, car adapter, and outlet power alternatives.

BRIEF DESCRIPTION OF DRAWINGS

The following figures form part of the present specification and are included to further demonstrate certain aspects of the present invention. The invention may be better understood by reference to one or more of these figures in combination with the detailed description of specific embodiments presented herein.

DETAILED DESCRIPTION

In the disclosure that follows, in the interest of clarity, not all features of actual implementations are described. It will of course be appreciated that in the development of any such actual implementation of the invention, as in any such project, numerous engineering and design decisions must be made to achieve the developers' specific goals and subgoals (e.g., compliance with mechanical and business-related constraints), which will vary from one implementation to another. While attention will necessarily be paid to proper engineering and design practices for the environment in question, and while such a development effort might be complex and time-consuming, a development effort would nevertheless be a routine undertaking for those of skill in the art given the benefit of this disclosure.

Figure 1:
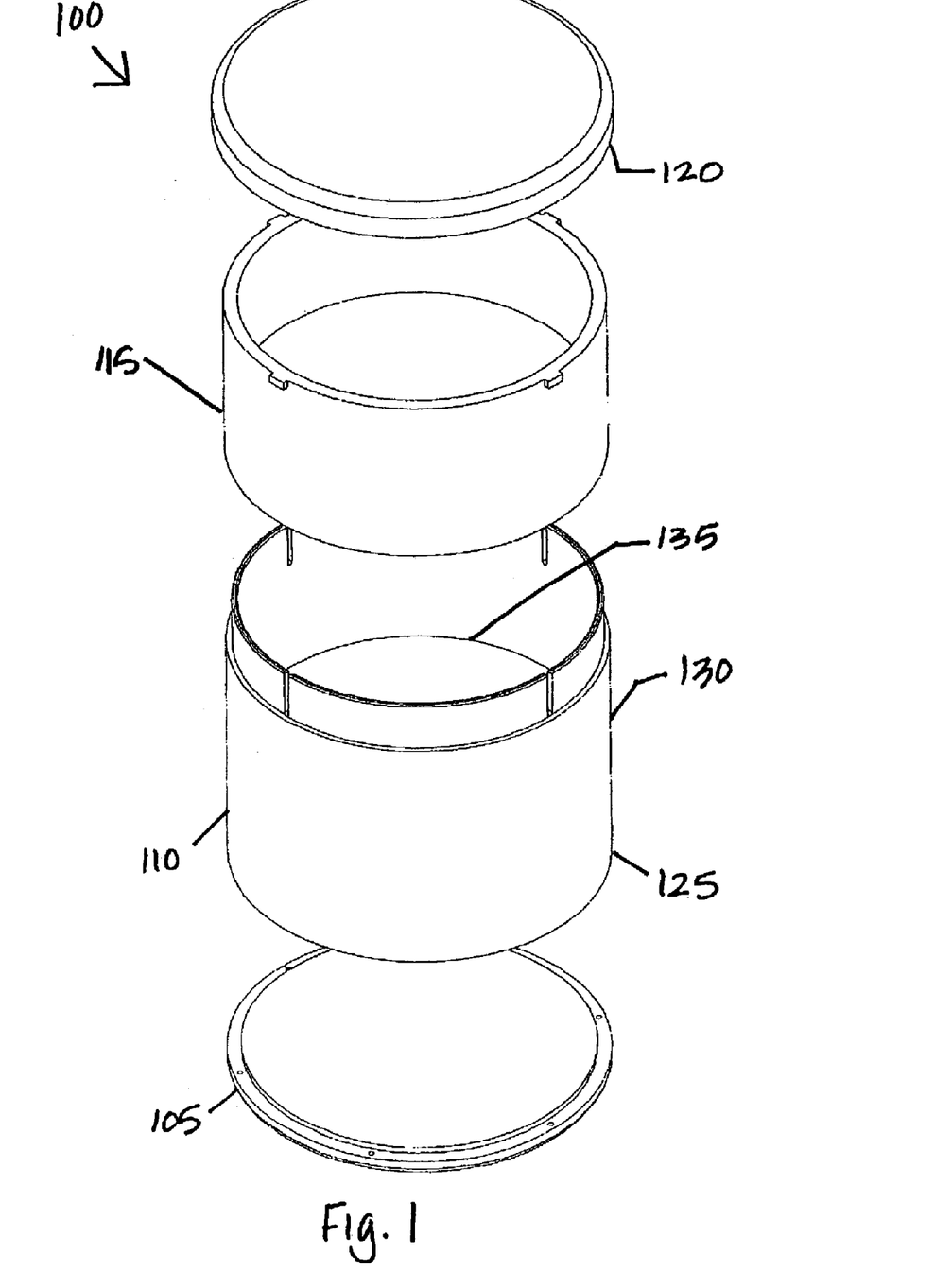
FIG. 1 depicts an exploded view of one embodiment of a hearing aid cleaning apparatus in accordance with the invention.

FIG. 1 depicts an embodiment of a hearing aid cleaning apparatus in accordance with the invention. Device 100 comprises bottom 105, body 110, desiccant compartment 115, and lid 120. Body 110 comprises a lower heating compartment 125, an upper hearing aid compartment 130, and dividing wall 135.

Figure 3:
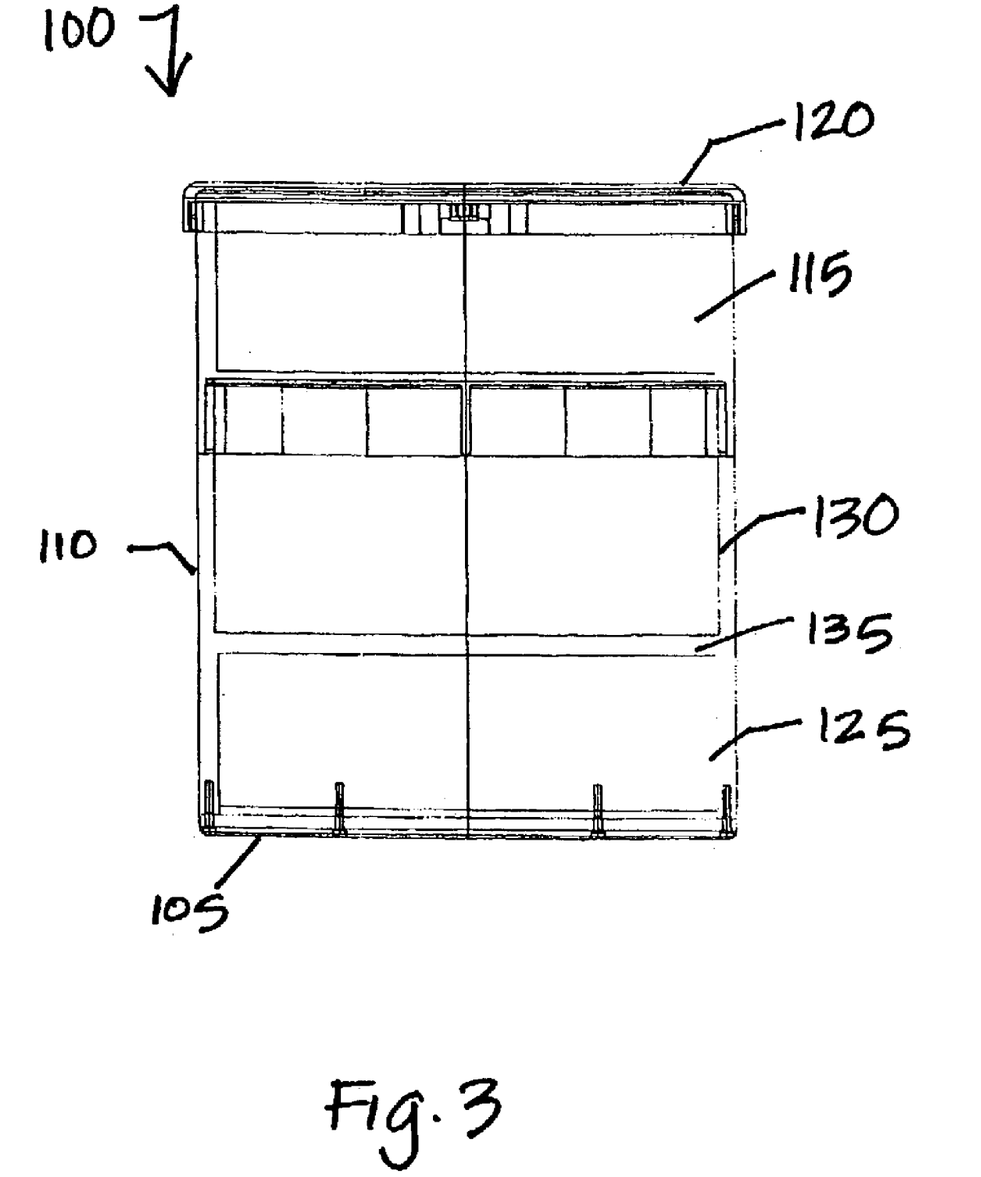
FIG. 3 depicts an assembled view of FIG. 1 exposing hidden features in accordance with the invention.

FIG. 3 depicts an assembled view of device 100 shown in FIG. 1 exposing hidden features in accordance with the invention. Three separate stacked compartments are visible in FIG. 3: heating compartment 125, hearing aid device compartment 130, and desiccant compartment 135.

Figure 2:
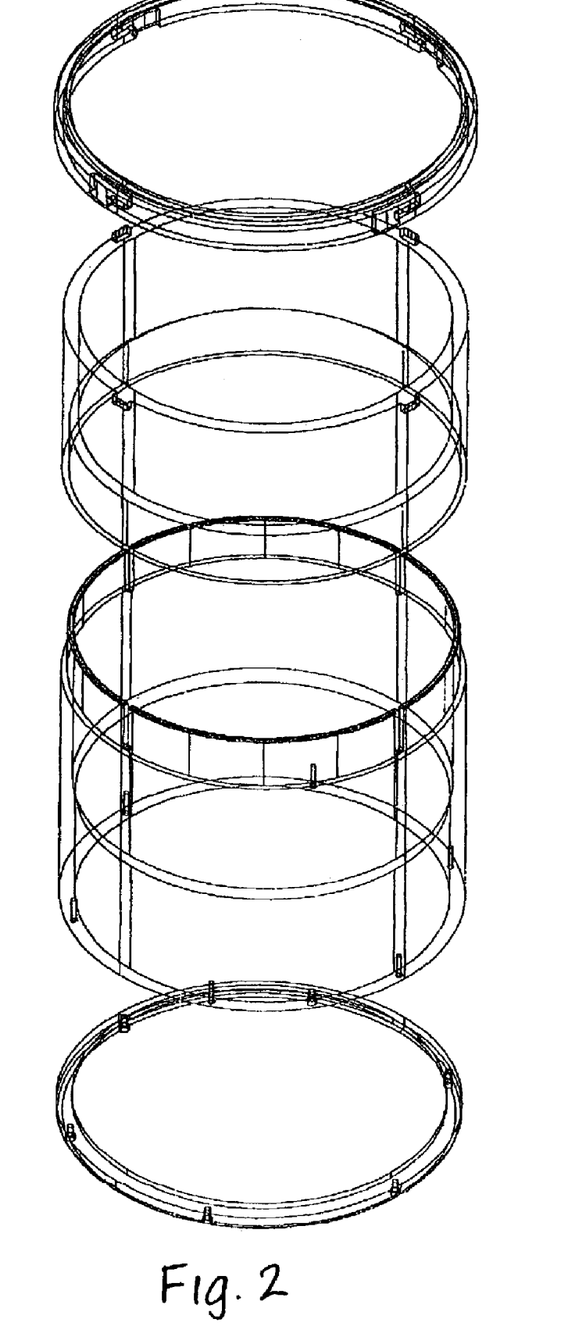
FIG. 2 depicts an alternative exploded view of FIG. 1, exposing hidden features in accordance with the invention.
Figure 4:
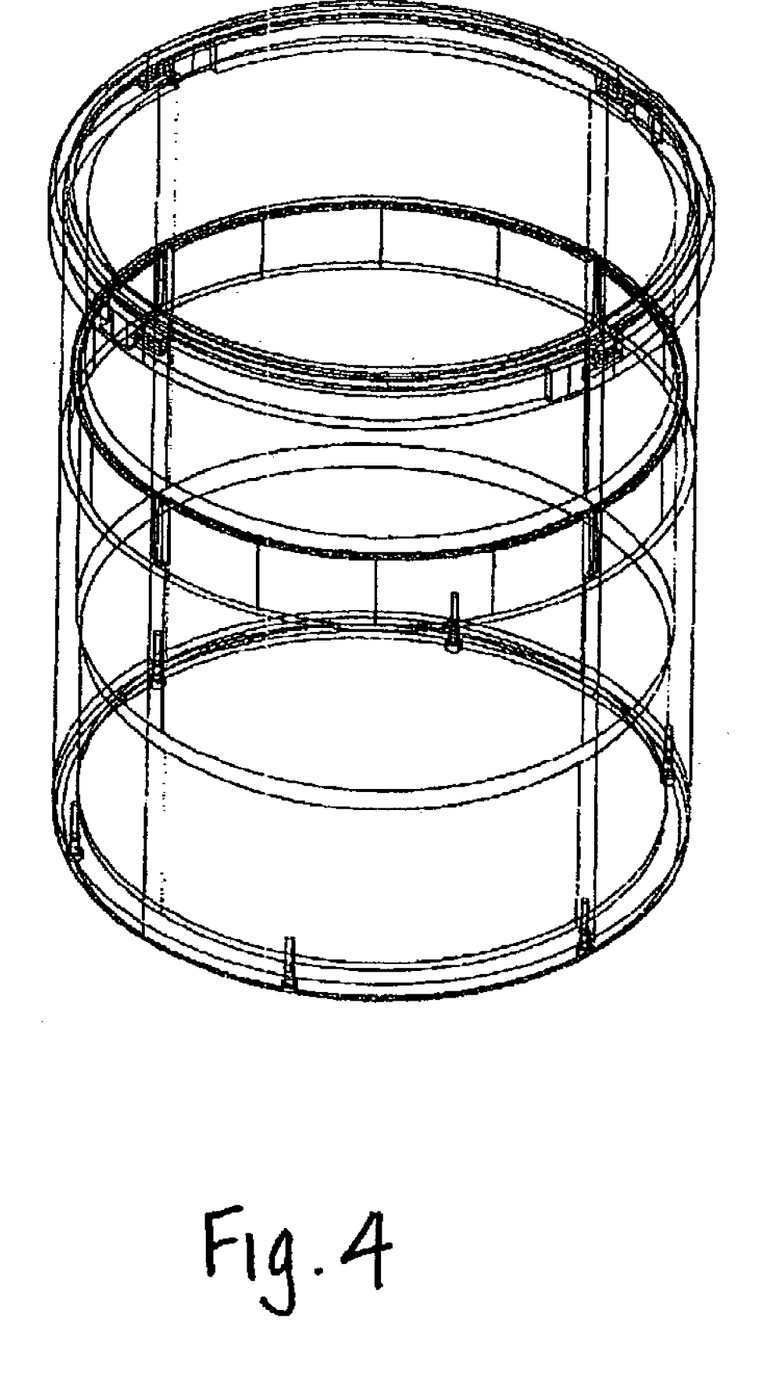
FIG. 4 depicts an alternative view of FIG. 3 exposing hidden features in accordance with the invention.

FIGS. 2 and 4, respectively, supplement FIGS. 1 and 3.

Hearing aid chamber 130 is essentially closed to external humidity when in operation. Desiccant chamber 115 is also essentially closed to external humidity when in operation. Heating element (not shown) is placed in a separate compartment from the hearing aid chamber or the desiccant chamber, i.e., heater compartment 125. The heat is transferred to hearing aid compartment 130 through conduction. As the wall of the lower compartment (heater compartment 125) warms, the moist air in the above hearing aid compartment 130 is stimulated through convection and subsequently rises into desiccant chamber 115. Such a configuration utilizes the natural force of physics and thus eliminates the need for a circulation style chamber. The ability to keep the moist air out of contact with the heating equipment, or the other electronic components can help prolong the life of the unit reducing or eliminating the chance of long term moisture damage and other potential damage caused by contact with ear wax or dirt/debris from the hearing aid or user.

The position of desiccant chamber 115 assists in more efficient removal of moisture because heat is directed upward along with the moisture. In addition, by avoiding circulation of a greater volume of gas or drawing outside air in, the invention prevents the circulation of moisturized air into the hearing aids and other electronic circuitry of device 100.

The desiccant (not shown) can be crystalline and can indicate its status, e.g., moisture changes the color of the desiccant. The desiccant can be within or separate from hearing aid chamber 130. It is desirable that the desiccant is exposed only to the hearing aid chamber.

Device 100 minimizes the volume of gas. The prior art relies on a circulation path, which requires a fan and an additional chamber; thus, creating a greater volume of air to dehumidify and a concomitant increase in the cost to produce and operate in terms of energy and desiccant.

Device 100 includes a heating element (not shown) which directs the heat upward into the hearing instrument chamber, and then into the desiccant (not shown). The desiccant can be stored in a separate chamber, or substantially in the same chamber as the hearing aid. In one embodiment, the desiccant can reside in a custom fit cavity, so as to expose the desiccant only to hearing aid chamber 130. The cavity can have a plurality of apertures (not shown) to allow gas flow between the chambers.

In one embodiment, device 100 can be set for continuous or pulse heat convection. Pulsed heat is an improvement over the prior art at least because it creates contraction and expansion cycles, contributing to the loosening of buildup. High temperature bursts for short periods of time are followed by cooling off periods. The heating and cooling cycle creates an expansion/contraction methodology that helps to loosen wax and moisture from the hearing instrument (not shown).

In one embodiment the heating/cooling cycle can be adjustable to enable for longer periods of heat for climates with higher humidity. In another embodiment device 100 will only enable the user to remove the hearing aids from hearing aid chamber 130 at the end of the cool cycle, thus preventing any chance of injury due to burns. The cool cycle allows the hearing aid to return to room temperature or at least substantially closer to body temperature. In another embodiment device 100 can include a cooling chamber or means of injecting cool gas to facilitate the contraction process.

In another embodiment device 100 can include an adjustable climate control—essentially a user controllable thermostat (not shown). Such an adjustment allows the device to reach higher temperatures and/or longer heating cycles for environments where the humidity is extreme. It is also beneficial for patients who also have an inordinate amount of perspiration or excessive moisture in or around the ear. The ability to reduce the amount of heat conveyed to the instrument, in the case of patients-with only mild moisture, helps to prevent over-drying the hearing aid. One of skill will recognize that excessive heat, applied over time to the hearing aid, may cause wires to become brittle, or the polyvinyl or other such receiver tubing to dry out and crack. Excessive drying may also cause the shell of the instrument, often made in part from softer materials (e.g. silicone or polyvinyl) to become hard prematurely. Also, tape is often used to hold wires inside the hearing aids, and excessive heat can cause loosening of the tape and eventually cause wires to shift causing shorts.

In another embodiment, device 100 includes an ionizer (not shown). Ionization assists in quickly removing moisture from hearing aid chamber 130. The byproduct of ionization is ozone, which helps to deodorize and/or disinfect the instrument. The anti-bacterial effect of ozone has been described in other hearing aid related patents, but only as a byproduct of UV (ultraviolet) radiation. Ionization can occur for either a single period, short periods or continuous operation. In another embodiment device 100 can include ozone or other such anti-bacterial gas (not shown), which will penetrate the inside of the hearing aid. In another embodiment an electrostatic force can be used to charge gas molecules.

The prior art relies on UV light to help kill bacteria. UV light may cause long term effects to the hearing aid shells which are quite often cured using Ultra Violet light. The continued use of UV lights may cause shells to become brittle over extended periods of exposure.

In another embodiment, device 100 can include a battery charger (not shown) for recharging batteries. In one embodiment the battery charger can be a separate attachment to device 100. Thus, a patient may avoid the often necessary purchase of hearing aid batteries or the patient may avoid an undesirable battery charger. In another embodiment the device includes a permanent or detachable unit for storing supporting supplies, e.g., wax brush/spare batteries (not shown), and for charging additional batteries. In another embodiment, device 100 can include a permanent or detachable holder for supplies and spare batteries.

In another embodiment, device 100 includes a vibrator (not shown) to help loosen buildup, making physical removal with a wax pick or wax brush easier.

In another embodiment, device 100 includes a continuous, pulsed, or temporary vacuum system (not shown) for removal of moist air molecules to assist the drying process.

In another embodiment, dividing wall 135 is covered by a custom fit, non-porous sleeve, e.g., rubber (not shown), exposing only the desiccant to hearing aid chamber 130. Thus, the desiccant is only required to dry the moisture in hearing aid chamber 130. A greater efficiency can be achieved when the desiccant is not required to dry the air in desiccant chamber 115, hearing aid chamber 130 and any other chamber.

In one embodiment, one or both desiccant chamber 115 and lid 120 are wholly or partially transparent, allowing desiccant status inspection without disassembly, including during the drying cycle. Such transparency supports indicating-type desiccant, which changes color as it becomes saturated. Thus, the introduction of humid air may be avoided by the user.

In another embodiment the desiccant can be accessed without exposing the gas in hearing aid chamber 130. In one embodiment lid 115 and desiccant chamber 120 can work to seal and unseal hearing aid chamber 130. In one such embodiment lid 120 can have downwardly extending arms, which, when lid 120 is twisted clockwise, work to press down on a seal in the floor of desiccant chamber 115 to unseat the seal (not shown), and when twisted counter-clockwise allow desiccant chamber 115 seal to reseat. Thus, moisturized air cannot enter hearing aid chamber 130. In another embodiment, a sleeve or retractable closing device between chambers (not shown) can be employed to prevent fresh, moist air from entering hearing aid chamber 130 when desiccant chamber 115 is accessed.

In another embodiment, the amount of desiccant inserted into desiccant chamber 115 by the patient is adjustable. The prior art only allows for a fixed volume of desiccant. By making the quantity adjustable, patients can use either more or less desiccant based on their environment; thus, removing a greater amount of moisture in a shorter period of time. This saves the patient money and/or it helps to keep hearing instruments dryer than previously existing methods.

In another embodiment, device 100 includes a centrifugal chamber or centrifugal support (not shown). The centrifugal action can be used to help direct wax out of the receiver port by introducing a force which helps to shake free recently embodied wax from the canal of the instrument. Orientation of the hearing aid will be instrumental ensuring that wax is forced out of the instrument, as opposed to into the receiver. The sound port will be positioned in a radial direction away from the center of the centrifuge.

In another embodiment, device 100 includes a charger (not shown), for charging the hearing aid sound port or tubing with an electrical stimulus. Such a stimulus is meant to help vibrate or electrically oppose the ear wax, assisting in forcing its migration from the instrument.

In another embodiment, device 100 includes a solar power supply. The solar power can be used to, for example, charge the batteries and/or to generate heat.

In another embodiment, device 100 includes a cooling chamber. Rapidly cooling hearing aid chamber 130 facilitates the contraction process, causing more rapid contraction of buildup and moisture.

In another embodiment, device 100 includes an alternative power supply utilizing battery power. Batteries allow for greater portability. The battery or batteries can be disposable or rechargeable.

Figure 5:
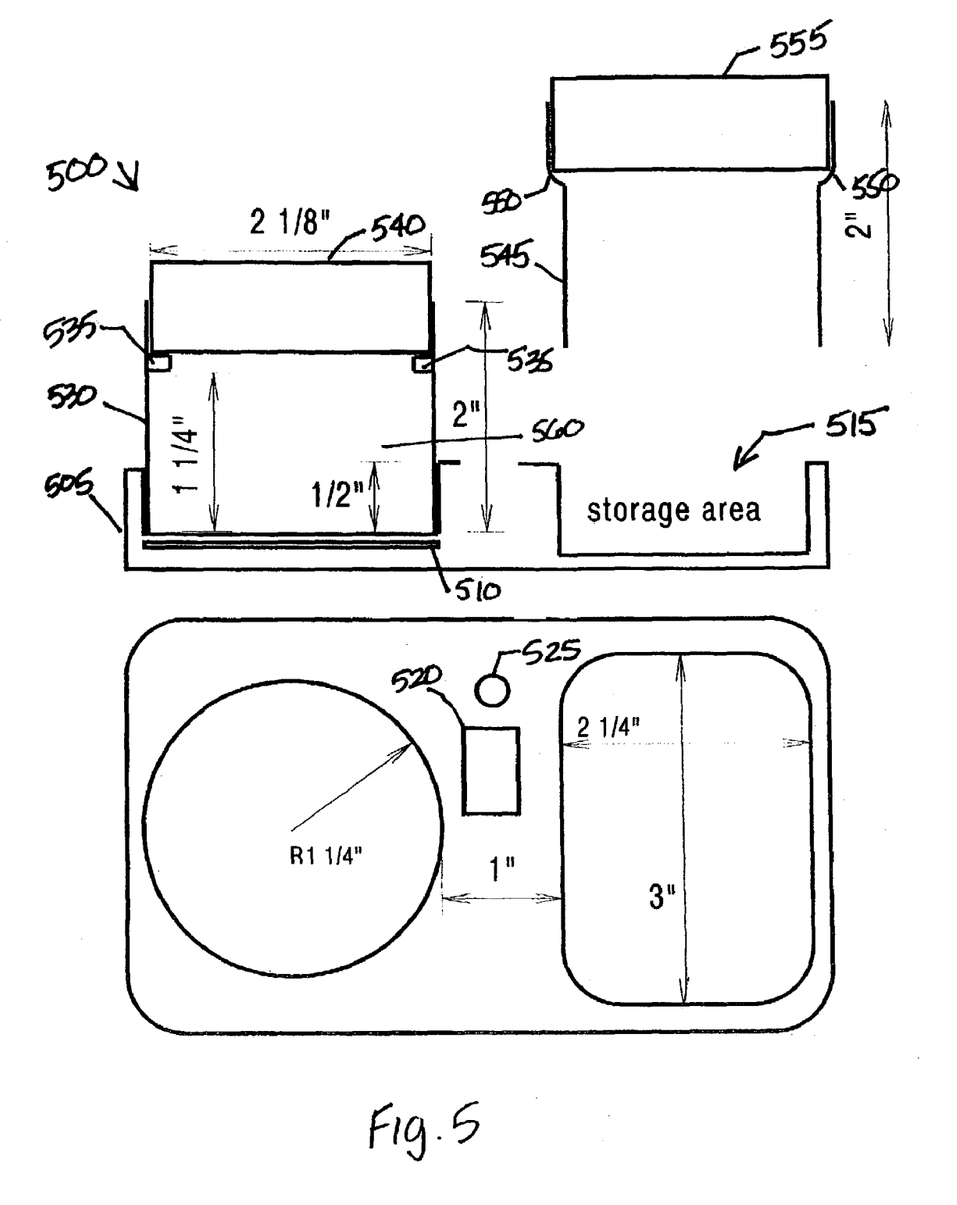
FIG. 5 depicts front cross section and top views of another embodiment of a hearing aid cleaning apparatus in accordance with the invention.

FIG. 5 depicts front cross section and top views of another embodiment of a hearing aid cleaning apparatus in accordance with the invention. The hearing aid cleaning and storage device 500 depicted in FIG. 5 includes, platform 505, heating element 510, storage area 515, switch 520, indicator lamp 525, chamber 530 having desiccant holders 535, desiccant 540, and spare chamber or enclosure 545 exhibiting alternative desiccant holders 550 with spare desiccant 555. When chamber 530 and desiccant 540 are in place, hearing aid device chamber 560 is essentially closed, having a fixed volume. Storage area 515 can hold spare items, cleaning utensils, or other items (not shown). Switch 520 is a manual on switch which can include a manual or automatic off feature. An automatic off feature, for example, could operate in conjunction with a sensor/circuitry monitoring time, humidity, and/or heat. Spare desiccant 555 would be kept in its package to prevent it from prematurely absorbing moisture.

In light of the above described components, a hearing aid cleaning apparatus can comprise a heater compartment containing a heating unit; a desiccant compartment containing desiccant material; and a hearing aid device (HAD) compartment. The heater-compartment is preferably connected to the HAD compartment. The desiccant compartment is preferably connected to the HAD compartment. Heat preferably can transfer from the heater compartment to the HAD compartment. Water vapor preferably can transfer from the HAD compartment to the desiccant compartment. Water vapor preferably cannot transfer from the HAD compartment to the heater compartment the heater compartment and the HAD compartment can be adjacent to each other, allowing conductive heating of the HAD compartment. Alternatively, the heater compartment and the HAD compartment can be connected by tubing, piping, or other mechanisms. If the two compartments are adjacent, then heat transfer can occur by conductive mechanisms. If the two compartments are not adjacent, then heat transfer can occur by flow of heated liquids or gases through the connecting mechanisms.

The desiccant compartment and the HAD compartment can be adjacent to each other. The two compartments can be connected by apertures, perforations, or other connectors. The two compartments can be connected by tubing, piping, or other mechanisms.

The desiccant compartment can generally be positioned in any orientation relative to the HAD compartment. It is presently preferred that the desiccant compartment be positioned above the HAD compartment. The heater compartment can generally be positioned in any orientation relative to the HAD compartment. It is presently preferred that the HAD compartment be positioned above the heater compartment.

The desiccant can generally be any type of desiccant. For ease of handling, it is presently preferred that the desiccant is a solid. It is possible to use non-solid desiccants such as gels, liquids, foams, or hydrogels. It is further preferable that the desiccant be a material that changes color upon absorbing water. In such a situation, it is preferable that the desiccant compartment be at least in part transparent so as to allow visual detection of the color of the desiccant. Examples of desiccants include montmorillonite clay, silica gel (silicon dioxide), indicating silica gel (silica gel impregnated with cobalt chloride—changes from blue to pink upon absorbing moisture), molecular sieves (porous crystalline aluminosilicates), calcium oxide, and calcium sulfate.

It is presently preferred that the desiccant compartment is capable of being closed to outside air when the HAD compartment is open to outside air. The apparatus can further comprise a closing mechanism capable of closing the connection between the desiccant compartment and the HAD compartment. This will reduce or minimize the entry of outside air into the desiccant compartment.

The closing mechanism can generally be any type of mechanism such as a door, rotating valve, iris valve, pinched connection, and so on.

The heating unit can generally be any type of heating unit such as an electric heater, chemical heater, or solar heater. The heating unit can be capable of delivering a single dose of heat, a pulsed dose of heat, or a continuous dose of heat to the HAD compartment.

The apparatus can also further comprise various elements. For example, the apparatus can further comprise an ionizing unit connected to the HAD compartment. The ionizing unit can be adjacent to the HAD compartment, or can be connected by tubing, piping, or the like. The ionizing unit can be capable of delivering a single dose of ionization, a pulsed dose of ionization, or a continuous dose of ionization to the HAD compartment. The ionizing unit can be capable of releasing ozone or an anti-bacterial gas to the HAD compartment.

The apparatus can be self-powered, or be connected to an external power unit. The apparatus can further comprise a battery or multiple batteries, a solar cell or solar cells, or electrical wiring for connection to an external power source (e.g. to a standard wall socket for 120 volt AC power). The apparatus can further comprise a power transformer.

The apparatus can further comprise a vibration unit. The vibration unit can be capable of delivering a single dose of vibration, a pulsed dose of vibration, or a continuous dose of vibration to the HAD compartment. The vibration can be accomplished through physical shaking, pulsed sound waves, and so on.

The apparatus can further comprise a cooling unit. The cooling unit can be connected to the HAD compartment. The cooling unit can be a powered cooling unit, a cooling sleeve, or other cooling mechanisms.

The apparatus can further comprise various other elements including a thermostat, a centrifuge unit, a handle or handles, a protective outer casing, labels, insignia, instructions, and so on. The apparatus can further comprise one or more cycle indicators. The indicators can be lights, rotating signs, beeps or other sounds, or other visual or auditory indicators. For example, the apparatus can comprise a heating cycle indicator light (e.g. red), a cooling cycle indicator light (e.g. blue), and a completed indicator light (e.g. green). These indicators can be conventional bulbs, light emitting diodes (LED), or other light sources.

The apparatus can be made from a variety of materials including plastics, metals, alloys, composites, ceramics, carbon fibers, graphite, and so on. Examples of plastics include ABS plastic and acrylics. Metals include steel, stainless steel, titanium, and aluminum. The apparatus can be made from one single material, or from a mixture of different materials. For example, the apparatus can be made of ABS plastic, with a clear acrylic window on the desiccant compartment.

The heater compartment, desiccant compartment, and HAD compartment can be fitted together in a variety of ways. For example, they can have a snap fit, a frictional fit, a screw fit, they can be held together using ridges or other projections that interconnect into matching receptors, they can have a magnetic fit, and so on.

The apparatus can be cleaned by ordinary soap and water, taking care not to damage the heating unit or other electronics. Depending on the materials use to construct the apparatus, isopropyl alcohol, ethanol, hydrogen peroxide, or other disinfectants could be used to further clean the apparatus.

The invention also includes methods of cleaning a hearing aid device using any of the above described apparatus. The method can comprise providing a hearing aid device, providing a hearing aid cleaning apparatus, placing the hearing aid in the HAD compartment, and closing the HAD compartment to outside air. The heating unit provides heat to the HAD compartment, and the desiccant material can absorb any moisture released from the hearing aid device.

The apparatus can be cycled through one or more cycles of heating and cooling. For example, it can be cycled through 1, 2, 3, 4, 5, 6, 7, 8, 9, 10, 11, or 12 cycles. The cooling cycles can comprise allowing the apparatus to cool to room temperature, or can comprise active cooling of the apparatus using a refrigerant or other mechanisms. The heating phase can comprise heating for about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, or ranges between any two of these values. It is presently preferred that the heating phase be about 20 minutes to about 30 minutes. The cooling phase can comprise cooling for about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, or ranges between any two of these values. It is presently preferred that the cooling phase be about 30 minutes to about 40 minutes, allowing the apparatus to approach room temperature. It is presently preferred that the apparatus go through about 8 cycles of heating and cooling.

The heating cycle preferably raises the temperature of the HAD compartment above about 100° F. (38° C.). It is presently preferred that the heating cycle brings the temperature of the HAD compartment to about 100° F. (38° C.) to about 140° F. (60° C.), and more preferably to about 100° F. (38° C.) to about 130° F. (54° C.). The cooling cycle preferably allows the apparatus to approach room temperature (variable depending on surroundings, typically about 70° F. (21° C.)).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Prototype Hearing Aid Cleaner Apparatus

A hearing aid cleaner apparatus as described above was constructed (see FIGS. 1–4). The prototype was prepared from ABS plastic, with a clear acrylic or Lucite window over the desiccant chamber to allow visual assay of the desiccant material.

The overall apparatus was cylinder-shaped, with a 3.25 inch outer diameter, a 3 inch inner diameter, and 3.75 inches in height (about the size of a typical coffee cup). Each of the heater compartment, HAD compartment, and desiccant compartment were about 1 inch in height. The HAD compartment was positioned over the heater compartment, and the desiccant compartment was positioned over the HAD compartment. Each compartment was machined to have a press/frictional fit with each other.

The desiccant compartment contained three receptacles for holding desiccant material. Three 2 gram canisters of CAN Sorb-It silica gel desiccant (commercially available from Sud-Chemie Performance Packaging, Albuquerque, N. Mex.) were placed in the receptacles.

The heating unit was a DC heating unit having a maximum temperature of 180° F. (82° C.). The apparatus was powered using a 9 volt DC transformer plugged into standard 120 volt AC current. The apparatus included a control timer, a heating unit, and an indicator light that indicated whether the heating unit was in a heating or cooling phase. Alternative designs include the attachment of a car cigarette lighter power source, or a mobile battery/batteries power source.

Example 2

Use of the Hearing Aid Cleaner Apparatus

The apparatus of Example 1 was used to clean a hearing aid device. The control timer was set to have eight cycles of heating and cooling. The heating phase lasted 20–30 minutes, and the temperature of the HAD compartment reached about 100–130° F. (38–54° C.). The control timer was not set to reach a specific temperature in the HAD compartment, although temperature control equipment could be readily installed (e.g. a thermostat or thermocouple). The cooling phase lasted about 40 minutes, and allowed the apparatus to return to room temperature. The prototype was not equipped with an active cooling mechanism, although one could be attached.

It is envisioned that the cycles of heating and cooling could readily be performed overnight while the user is asleep (the total cycle time is about eight hours).

All of the methods and/or apparatus disclosed and claimed herein can be made and executed without undue experimentation in light of the present disclosure. While the methods and apparatus of this invention have been described in terms of preferred embodiments, it will be apparent to those of skill in the art that variations may be applied to the methods and/or apparatus and in the steps or in the sequence of steps of the methods described herein without departing from the concept and scope of the invention. More specifically, it will be apparent that certain agents which are chemically related may be substituted for the agents described herein while the same or similar results would be achieved. All such similar substitutes and modifications apparent to those skilled in the art are deemed to be within the scope and concept of the invention.

The invention claimed is:

1. A hearing aid cleaning apparatus comprising:
    a heater compartment containing a heating unit;
    a desiccant compartment containing desiccant material; and
    a hearing aid device (HAD) compartment; wherein:
        the heater compartment is connected to the HAD compartment;
        the desiccant compartment is connected to the HAD compartment;
        heat can transfer from the heater compartment to the HAD compartment;
        water vapor can transfer from the HAD compartment to the desiccant compartment; and
        the heater compartment is separate from the desiccant compartment and from the HAD compartment such that air or gas cannot circulate between the HAD compartment and the heater compartment.

2. The apparatus of claim 1, wherein the heater compartment and the HAD compartment are adjacent to each other.

3. The apparatus of claim 1, wherein the desiccant compartment and the HAD compartment are adjacent to each other.

4. The apparatus of claim 3, wherein the desiccant compartment and the HAD compartment are connected by apertures or perforations.

5. The apparatus of claim 1, wherein the desiccant compartment and the HAD compartment are connected by tubing or piping.

6. The apparatus of claim 1, wherein the HAD compartment is positioned above the heater compartment.

7. The apparatus of claim 1, wherein the desiccant compartment is positioned above the HAD compartment.

8. The apparatus of claim 1, wherein:
the HAD compartment is positioned above the heater compartment; and
the desiccant compartment is positioned above the HAD compartment.

9. The apparatus of claim 1, wherein the desiccant compartment is closed to outside air when the HAD compartment is open to outside air.

10. The apparatus of claim 1, further comprising a closing mechanism wherein placing the closing mechanism in a closed position closes the connection between the desiccant compartment and the HAD compartment.

11. The apparatus of claim 1, wherein the heating unit comprises a heating unit selected from the group consisting of a single dose generating heating unit, a pulsed dose generating heating unit, and a continuous dose generating heating unit.

12. The apparatus of claim 1, further comprising an ionizer connected to the HAD compartment.

13. The apparatus of claim 12, wherein the ionizer is selected from the group consisting of a single dose of ionization generating ionizer, a pulsed dose of ionization generating ionizer, or a continuous dose of ionization generating ionizer.

14. The apparatus of claim 12, wherein the ionizer releases ozone or an anti-bacterial gas to the HAD compartment.

15. The apparatus of claim 1, further comprising a power unit.

16. The apparatus of claim 15, wherein the power unit comprises a battery, a solar cell, or electrical wiring.

17. The apparatus of claim 1, further comprising a vibration unit.

18. The apparatus of claim 17, wherein the vibration unit comprises a vibration unit selected from the group consisting of a single dose of vibration generating vibrator, a pulsed dose of vibration generating vibrator, or a continuous dose of vibration generating vibrator.

19. The apparatus of claim 1, further comprising a cooling unit connected to the HAD compartment.

20. The apparatus of claim 1, further comprising a thermostat connected to the heating unit.

21. The apparatus of claim 1, further comprising a centrifuge unit.

22. The apparatus of claim 1, wherein the desiccant material is a solid.

23. The apparatus of claim 1, wherein the desiccant material changes color upon absorbing water.

24. The apparatus of claim 1, wherein the desiccant compartment comprises a transparent material.

25. The apparatus of claim 1, wherein the desiccant material compartment comprises a transparent plastic material.

26. A method for cleaning a hearing aid, the method comprising:
providing a hearing aid;
providing a hearing aid cleaning apparatus comprising a heater compartment containing a heating unit, a desiccant compartment containing a desiccant material, and a hearing aid device (HAD) compartment wherein the desiccant compartment is connected to the HAD compartment such that water vapor can transfer from the HAD compartment to the desiccant compartment, and the heater compartment is separate from the desiccant compartment and from the HAD compartment, such that air or gas or debris cannot circulate between the HAD compartment and the heater compartment;
placing a hearing aid in the HAD compartment;
closing the HAD compartment to outside air; and
activating the heating unit to remove moisture from the hearing aid.

27. An apparatus for cleaning a hearing aid device, comprising:
a hearing aid compartment for receiving a hearing aid device;
a desiccant compartment containing a desiccant, the desiccant compartment connected to the hearing aid compartment to permit air or gas to flow between the desiccant compartment and the hearing aid compartment;
a heater compartment containing a heating unit for heating the hearing aid compartment, the heater compartment separate from the hearing aid compartment and the desiccant compartment such that air or gas or debris cannot circulate between the heater compartment and the hearing aid compartment; and
a wall between the heater compartment and the hearing aid compartment;
wherein heat is transferred from the heating compartment to the hearing aid compartment by conduction through the wall.

28. An apparatus for cleaning a hearing aid device, comprising:
a heater compartment containing a heating unit;
a hearing aid compartment for receiving a hearing aid device, the hearing aid compartment positioned above the heater compartment; and
a desiccant compartment containing a desiccant, the desiccant compartment positioned above the hearing aid compartment;
wherein the desiccant compartment is connected to the hearing aid compartment to permit air or gas to flow between the desiccant compartment and the hearing aid compartment by convection, and the heater compartment is separate from the hearing aid compartment and the desiccant compartment such that air or gas or debris cannot circulate between the heater compartment and the hearing aid compartment.

29. The apparatus of claim 28, further comprising a wall between said heater compartment and said hearing aid compartment, wherein heat is transferred from said heating compartment to said hearing aid compartment by conduction through said wall.

* * * * *